United States Patent
Krill et al.

(10) Patent No.: US 10,343,980 B2
(45) Date of Patent: Jul. 9, 2019

(54) PREPARATION OF N,N-(DI)ALKYLAMINOALKYL(METH)-ACRYLAMIDE OR N,N-(DI)ALKYLAMINOALKYL (METH)ACRYLATE AND THE QUATERNARY AMMONIUM SALTS THEREOF AS FLOCCULATING AIDS AND GELLING AGENTS

(71) Applicant: Evonik Roehm GmbH, Darmstadt (DE)

(72) Inventors: Steffen Krill, Muehltal (DE); Patrik Hartmann, Buettelborn (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/624,924

(22) Filed: Jun. 16, 2017

(65) Prior Publication Data
US 2017/0369424 A1 Dec. 28, 2017

(30) Foreign Application Priority Data

Jun. 28, 2016 (EP) ..................................... 16176555

(51) Int. Cl.
| | | |
|---|---|---|
| C07C 233/38 | (2006.01) | |
| C07C 231/02 | (2006.01) | |
| C08F 220/60 | (2006.01) | |
| C07C 213/06 | (2006.01) | |

(52) U.S. Cl.
CPC .......... *C07C 233/38* (2013.01); *C07C 213/06* (2013.01); *C07C 231/02* (2013.01); *C08F 220/60* (2013.01)

(58) Field of Classification Search
CPC ... C07C 233/38; C07C 213/06; C07C 231/02; C08F 220/60
See application file for complete search history.

(56) References Cited

U.S. PATENT DOCUMENTS

| | | |
|---|---|---|
| 4,605,740 A | 8/1986 | Landscheidt |
| 5,292,950 A | 3/1994 | Oka et al. |
| 6,437,173 B1 * | 8/2002 | Hurtel .................. C07C 213/06 560/217 |
| 8,674,133 B2 | 3/2014 | Schmitt et al. |
| 2005/0124529 A1 * | 6/2005 | Liu ........................ C07C 233/38 510/499 |
| 2008/0234515 A1 | 9/2008 | Liu |
| 2011/0313195 A1 | 12/2011 | Schmitt et al. |

FOREIGN PATENT DOCUMENTS

| | | |
|---|---|---|
| DE | 10 2009 002 239 A1 | 10/2010 |
| EP | 0 117 530 B1 | 3/1989 |
| EP | 0419654 A1 | 4/1991 |
| EP | 0 960 877 A2 | 12/1999 |
| EP | 0 968 995 B1 | 8/2002 |
| WO | WO 99/25394 A2 | 5/1999 |
| WO | WO 03/101935 A1 | 12/2003 |

OTHER PUBLICATIONS

Anqiang Zhang, et al. "Synthesis and antimicrobial activities of acrylamide polymers containing quaternary ammonium salts on bacteria and phytopathogenic fungi," Reactive and Functional Polymers, vol. 88, XP029214105A, 2015, pp. 39-46.
Singapore Search Report issued in corresponding application No. 10201705219Q, dated Mar. 27, 2018.

* cited by examiner

*Primary Examiner* — Peter D. Mulcahy
(74) *Attorney, Agent, or Firm* — Grüneberg and Myers PLLC

(57) ABSTRACT

N,N-(di)alkylaminoalkyl(meth)acrylamide or N,N-(di)alkylaminoalkyl (meth)acrylate and/or a quaternary ammonium salt thereof are prepared with a low content of a compound of formula (IV)

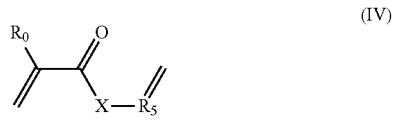

(IV)

wherein $R_5$ in each case is a linear, branched or cyclic alkyl radical, an aryl radical which may also be substituted by one or more alkyl groups, the linear, cyclic or branched alkyl radical may have a length of 1-12 carbon atoms and is, for example, methyl, ethyl, propyl, isopropyl, butyl, isobutyl, tert-butyl, pentyl, hexyl, heptyl, octyl, isooctyl, nonyl, decyl, undecyl, dodecyl.

14 Claims, No Drawings

PREPARATION OF N,N-(DI)ALKYLAMINOALKYL(METH)-ACRYLAMIDE OR N,N-(DI)ALKYLAMINOALKYL (METH)ACRYLATE AND THE QUATERNARY AMMONIUM SALTS THEREOF AS FLOCCULATING AIDS AND GELLING AGENTS

BACKGROUND OF THE INVENTION

Field of the Invention

The present invention describes a process for preparing N,N-(di)alkylaminoalkyl(meth)acrylamide or N,N-(di)alkylaminoalkyl (meth)acrylate and the quaternary ammonium salts thereof with a low content of the compounds corresponding to the formula (IV).

Description of the Related Art

The preparation of dimethylaminopropylmethacrylamide (DMAPMA) is known from the related art.

EP 0 960 877 (Elf Atochem S.A.) describes a continuous process for preparing methacrylate esters of dialkylamino alcohols. Dialkylamino alcohols are reacted with generally methyl (meth)acrylate, and the dialkylaminoalkyl (meth) acrylate is obtained by the following method:

The mixture of the starting materials (methyl (meth) acrylate and dialkylamino alcohol) is supplied continuously to a stirred reactor together with a tetraalkyl titanate as catalyst (for example tetrabutyl, tetraethyl or tetra(2-ethylhexyl) titanate) and at least one polymerization inhibitor (for example phenothiazine, tert-butylcatechol, hydroquinone monomethyl ether or hydroquinone), where the conversion to the dialkylamino (meth)acrylate is effected at a temperature of 90° C.-120° C. with simultaneous continuous removal of the azeotropic methyl (meth)acrylate/methanol mixture. The crude reaction mixture (crude ester) is fed to a first distillation column, wherein an essentially catalyst-free stream is drawn off at the top of the distillation column under reduced pressure and the catalyst and a little dialkylaminoalkyl (meth)acrylate are drawn off at the bottom of the distillation column. The top stream from the first distillation column is then fed to a second distillation column in which, under reduced pressure, a stream of low-boiling products comprising a little dialkylaminoalkyl (meth)acrylate is drawn off at the top and a stream consisting of mainly dialkylaminoalkyl (meth)acrylate and polymerization inhibitor(s) is drawn off at the bottom and is supplied to a third distillation column. In the third distillation column, under reduced pressure, a rectification is conducted, in which the desired pure dialkylaminoalkyl (meth)acrylate is drawn off at the top and essentially the polymerization inhibitor(s) at the bottom. After further purification with the aid of a film evaporator, the bottom stream from the first distillation column is recycled into the reactor, just like the top stream from the second distillation column.

This process dispenses with dewatering of the alcohols before use, which can lead to increased deactivation of the tetraalkyl titanate used owing to hydrolysis that extends as far as formation of unwanted solid deposits. Furthermore, the process has the disadvantage that the catalyst is subjected to thermal stress at relatively high temperatures in the bottom of the first distillation column. This can easily lead to breakdown of the catalyst.

In this process, there are a total of two overhead rectifications both of the unconverted reactants and of the product. This entails very high energy costs and a total of 4 rectification columns, some of which have to have very large dimensions. The process is therefore afflicted with very high capital and operating costs.

EP 0 968 995 (Mitsubishi Gas Chemical Comp.) describes a continuous process for preparing alkyl (meth)acrylates using a reaction column. The transesterification reaction is effected here directly in a distillation column (i.e. reactor and distillation column for removal of methyl (meth)acrylate/methanol azeotrope form one apparatus), which is supplied continuously with the starting materials (methyl (meth) acrylate and alcohol). The necessary catalyst, here likewise preferably a titanium compound, is present in the distillation column. In the case of a homogeneous catalyst, the catalyst is metered continuously into the distillation column. However, the use of homogeneous catalysts in a distillation column, because of the flushing effect resulting from the liquid reflux in the distillation column, leads to elevated catalyst demand and, in the event of occurrence of solid catalyst precipitation, to soiling of the column internals. In the case of a heterogeneous catalyst, the catalyst is in the reaction column. However, the positioning of the catalyst in the distillation column is disadvantageous because an elevated pressure drop then occurs in the distillation column and, in addition, a very high level of cost and inconvenience is necessary for the regular cleaning of the distillation column. Moreover, heterogeneous catalysts can become deactivated, for example as a result of unwanted polymerization.

U.S. Pat. No. 8,674,133 (Evonik Röhm GmbH) describes a continuous process for preparing alkylamino(meth)acrylamides by means of continuous aminolysis. The reduction in the crosslinker content is achieved here via complex processing steps, especially distillations.

The above-described processes lead to the formation of various by-products, most of which cannot remain in the end product. The removal of the by-products leads to the known disadvantages, for example yield losses and elevated capital, operating and maintenance costs as a result of the purification steps required.

SUMMARY OF THE INVENTION

In the synthesis of N,N-(di)alkylaminopropylmethacrylamides and the quaternary ammonium salts thereof, the formation of compounds of the formula (IV)

(IV)

is particularly undesirable. An elevated proportion of this compound in the end product leads to premature and uncontrolled crosslinking in the polymerization.

The problem addressed was that of providing a process with which N,N-(di)alkylaminoalkyl(meth)acrylamides or N,N-(di)alkylaminoalkyl (meth)acrylate and the quaternary ammonium salts thereof can be prepared with a low content of compounds of the formula (IV). Another problem addressed was that of providing a process for preparing monomers which enables the preparation of soluble or non-coagulating polymers.

The problem was solved by a process for preparing N,N-(di)alkylaminoalkyl(meth)acrylamide or N,N-(di)alkylaminoalkyl (meth)acrylate of the general formula (I)

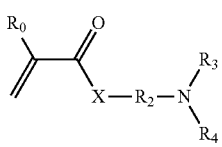

where
R⁰ is hydrogen or methyl
X is NH or O
$R_2$, $R_3$, $R_4$ are each a linear, branched or cyclic alkyl radical, an aryl radical which may also be substituted by one or more alkyl groups, the linear, cyclic or branched alkyl radical may have a length of 1-12 carbon atoms and is, for example, methyl, ethyl, propyl, isopropyl, butyl, isobutyl, tert-butyl, pentyl, hexyl, heptyl, octyl, isooctyl, nonyl, decyl, undecyl, dodecyl, having a content of less than 1200 ppm of the compound (IV) of the general formula

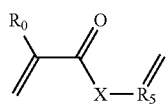

where $R_5$ in each case is a linear, branched or cyclic alkyl radical, an aryl radical which may also be substituted by one or more alkyl groups, the linear, cyclic or branched alkyl radical may have a length of 1-12 carbon atoms and is, for example, methyl, ethyl, propyl, isopropyl, butyl, isobutyl, tert-butyl, pentyl, hexyl, heptyl, octyl, isooctyl, nonyl, decyl, undecyl, dodecyl, characterized in that the oxygen concentration is <1000 ppm in the liquid phase in at least one component step of the preparation.

The problem was solved by a process for preparing N,N-(di)alkylaminoalkyl(meth)acrylamide or N,N-(di)alkylaminoalkyl (meth)acrylate of the general formula (I) and the quaternary ammonium salts thereof having a content of compounds of the formula (IV) of less than 1200 ppm, characterized in that operation is effected with a reduced oxygen content.

The content of the compounds of formula (IV) is preferably less than 1000 ppm, more preferably less than 850 ppm, most preferably less than 700 ppm.

The notation "(meth)acrylate" here means both methacrylate, for example methyl methacrylate, ethyl methacrylate, etc., and acrylate, for example methyl acrylate, ethyl acrylate, etc., and mixtures of the two.

The problem was also solved by a process for preparing N,N-(di)alkylaminoalkyl(meth)acrylamide or N,N-(di)alkylaminoalkyl (meth)acrylate according to Claim 1 having a content of less than 1200 ppm of the compound of the formula (IV) or quaternary ammonium salts thereof which are used for preparation of soluble or non-coagulating polymers.

Soluble or non-coagulating polymers in this context means that the N,N-(di)alkylaminoalkyl(meth)acrylamides or N,N-(di)alkylaminoalkyl (meth)acrylates prepared in accordance with the invention, after polymerization or copolymerization with other compounds, can be brought into solution in a suitable solvent or form a non-coagulating emulsion or dispersion. It is likewise possible for the N,N-(di)alkylaminoalkyl(meth)acrylamides or N,N-(di)alkylaminoalkyl (meth)acrylates quaternized in accordance with the invention, after polymerization or copolymerization, to be brought into solution in suitable solvents.

DETAILED DESCRIPTION OF THE INVENTION

It has been found that, surprisingly, the formation of compounds of the formula (IV) can be minimized by the reduction of the oxygen level in the reaction system.

The reduction of the oxygen level means that, in the preparation of N,N-(di)alkylaminoalkyl(meth)acrylamide or N,N-(di)alkylaminoalkyl (meth)acrylate, the oxygen concentration is <1000 ppm in the liquid phase in at least one component step. Preferably, the oxygen concentration is less than 1000 ppm in the liquid phase in the conversion of the reactants in the reaction vessel or the stirred tank cascade.

Ideally, the reaction is conducted with exclusion of oxygen. The reaction can be conducted either under vacuum or under a protective gas atmosphere, for example under an $N_2$ or argon atmosphere.

It has been found that the reduction in the residence time can also contribute to the reduction of the formation of compounds of the formula (IV). A reduction in the residence time without a considerable reduction in the space-time yield can be achieved via the following measures:
  use of more active catalysts,
  use of elevated amounts of catalyst,
  a shift in equilibrium as a result of increased alcohol removal, for example by virtue of higher column capacities and/or more energy input.

It has been found that, surprisingly, the reduction in the reaction temperature also leads to a reduction in the content of compounds of formula (IV). In order to avoid the high temperatures that are customary in the process at the end of the reaction, the pressure is reduced at the same time. The reduction in the pressure in the reaction is preferably effected toward the end of the reaction. Accordingly, the pressure at the start of the reaction can also be increased.

The process for preparing N,N-(di)alkylaminoalkyl(meth)acrylamides or N,N-(di)alkylaminoalkyl (meth)acrylate comprises the aminolysis or alcoholysis of alkyl (meth)acrylates with amines or alcohols with release of alcohols.

The (meth)acrylate feed reactant is supplied continuously to a suitable reaction apparatus, it being possible to use either an individual reaction vessel or a cascade of two or more reaction vessels connected in series. Such a cascade may consist, for example, of 2, 3, 4, 5, 6 or optionally several individual reaction vessels. In a preferred embodiment, a cascade of 3 continuously operated stirred tanks arranged in series is used.

The (meth)acrylate feed reactant can be effected in various ways. It is possible, for example, to feed a reactant stream only to the first reaction vessel of the cascade or else to divide the reactant stream into substreams and to supply these substreams to all or just some of the series-connected reaction vessels of the cascade. It is likewise possible to undertake the feeding of the reactant stream via the low boiler discharge distillation column and/or the reaction apparatuses. It may be advantageous to feed the reactant stream only into the low boiler discharge distillation column or, in a further embodiment, to divide the reactant stream into substreams which are then supplied either to the low boiler discharge distillation column or to the first or optionally two or more reaction vessels of the cascade.

Suitable alkyl (meth)acrylates are compounds of the formula (II)

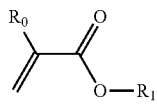

where
R₀ is hydrogen or methyl
R₁ is linear or branched alkyl radical having 1 to 10, preferably 1 to 4, carbon atoms.

Typical examples of these are methyl (meth)acrylate, ethyl (meth)acrylate, propyl (meth)acrylate, isopropyl (meth)acrylate, n-butyl (meth)acrylate, isobutyl (meth)acrylate, 3-methylbutyl (meth)acrylate, amyl (meth)acrylate, neopentyl (meth)acrylate, hexyl (meth)acrylate, cyclohexyl (meth)acrylate, heptyl (meth)acrylate, n-octyl (meth)acrylate, ethylhexyl (meth)acrylate or decyl (meth)acrylate.

It is advisable that all reaction vessels have a vapour draw to the distillation column for removal of the alcohol released in the reaction.

In particular embodiments, it has been found to be advantageous to introduce the discharge from one tank of the cascade into the bottom of the next tank of the cascade downstream in each case.

The reactant is supplied continuously to the low boiler discharge distillation column for dewatering.

Suitable reactants are compounds of the formula (III)

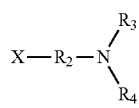

with
X=OH or NH₂
R₂, R₃, R₄ each a linear, branched or cyclic alkyl radical, an aryl radical which may also be substituted by one or more alkyl groups, the linear, cyclic or branched alkyl radical may have a length of 1-12 carbon atoms and is, for example, methyl, ethyl, propyl, isopropyl, butyl, isobutyl, tert-butyl, pentyl, hexyl, heptyl, octyl, isooctyl, nonyl, decyl, undecyl, dodecyl.

Examples of useful reactants include the following compounds:
dimethylaminoethylamine, diethylaminoethylamine, dipropylaminoethylamine, diisopropylaminoethylamine, dibutylaminoethylamine, disobutylaminoethylamine, dimethylaminopropylamine, diethylaminopropylamine, dipropylaminopropylamine, diisopropylaminopropylamine, dibutylaminopropylamine, disobutylaminopropylamine, dimethylaminobutvlamine, diethylaminobutylamine, dipropylaminobutylamine, diisopropylaminobutylamine, dibutylaminobutylamine, disobutylaminobutylamine, dimethylaminohexylamine, diethylaminohexylamine, dimethylaminoneopentylamine, methylethylaminopropylamine, methylpropylaminopropylamine, methylpropylaminoethylamine, methylethylaminoethylamine, dimethylaminoethyl alcohol, diethylaminoethyl alcohol, dipropylaminoethyl alcohol, diisopropylaminoethyl alcohol, dibutylaminoethyl alcohol, disobutylaminoethyl alcohol, dimethylaminopropyl alcohol, diethylaminopropyl alcohol, dipropylaminopropyl alcohol, diisopropylaminopropyl alcohol, dibutylaminopropyl alcohol, disobutylaminopropyl alcohol, dimethylaminobutyl alcohol, diethylaminobutvl alcohol, dipropylaminobutyl alcohol, diisopropylaminobutyl alcohol, dibutylaminobutyl alcohol, disobutvlaminobutyl alcohol, dimethylaminohexyl alcohol, diethylaminohexyl alcohol, dimethylaminoneopentyl alcohol, methylethylaminopropyl alcohol, methylpropylaminopropyl alcohol, methylpropylaminoethyl alcohol, methylethylaminoethyl alcohol.

Particular preference is given to dimethylaminopropylamine, dimethylaminoethylamine, dimethylaminohexylamine, dimethylaminopropyl alcohol, dimethylaminoethyl alcohol, and dimethylaminohexyl alcohol.

Catalysts and polymerization inhibitors are likewise preferably metered continuously into the reaction apparatus.

Transesterification catalysts used may be any catalysts known from the related art.

Useful catalysts include, for example, zirconium acetylacetonate and further 1,3-diketones of zirconium; in addition, it is possible to use mixtures of alkali metal cyanates or alkali metal thiocyanates and alkali metal halides, and also tin compounds, for example dioctyltin oxide, alkaline earth metal oxides or alkaline earth metal hydroxides, for example LiOH, CaO, Ca(OH)₂, MgO, Mg(OH)₂, or mixtures of the aforementioned compounds, and also alkali metal hydroxides, alkali metal alkoxides and lithium chloride and lithium hydroxide; it is also possible to use mixtures of the aforementioned compounds with the aforementioned alkaline earth metal compounds and lithium salts, especially lithium chloride and calcium hydroxide, dialkyltin oxides, for example dioctyltin oxide, alkali metal carbonates, alkali metal carbonates together with quaternary ammonium salts, for example tetrabutylammonium hydroxide or hexadecyltrimethylammonium bromide, and also mixed catalysts composed of diorganyltin oxide and organyltin halide, acidic ion exchangers, phosphorus-molybdenum heteropolyacids, titanium alkoxides, for example isopropyl titanate, chelate compounds of the metals titanium, zirconium, iron or zinc with 1,3-dicarbonyl compounds, lead compounds, for example lead oxides, lead hydroxides, lead alkoxides, lead carbonates or lead salts of carboxylic acids, and alkaline earth metal amides, especially lithium amide. Likewise suitable are alkali metal alkoxides, preferably lithium alkoxides, especially lithium methoxide. Particular preference is given to a catalyst mixture composed of dialkyltin oxide and alkyl titanate, for example dioctyltin oxide and isopropyl titanate, in a ratio of about 1:3 (% by weight) to 3:1 (% by weight). The catalyst mixture is used in amounts of 0.1%-10% by weight, based on the amount of the reactants used.

Pre-activation of the catalyst has been found to be advantageous. This involves mixing or dispersing the catalysts, heating them to temperatures of 90° C. to 120° C. and stirring them for 2 to 3 h until a homogeneous clear solution has formed.

Examples of useful polymerization inhibitors include hydroquinone, hydroquinone monomethyl ether and the piperidyl derivatives.

The reduction in the oxygen level may require that the stabilizers requiring oxygen that are typically used be replaced by stabilizers that work in an oxygen-free manner.

Preference is given to polymerization inhibitors selected from the group of bis(2-methoxycarbonylpropyl) sulphide, N,N-diethylhydroxylamine, phenothiazine, 4-hydroxy-2,2,6,6-tetramethylpiperidinooxyl or N,N'-diphenyl-p-phenylenediamine and derivatives thereof (for example esters, amides etc.).

The choice of the starting materials is particularly advantageously made such that it is possible to shift the equilibrium to the side of the products with the removal of the alcohol from the reaction mixture. The removal of the alcohol can be effected by distillation by virtue of its lower boiling point compared to the reactant used and/or through the formation of an azeotrope.

The reactant used may contain water. The amount of water in the reactant used is below 5000 ppm. Before it enters the reaction apparatus, the reactant is dewatered by distillation, preferably by means of a distillation column. This involves drawing off the water present in the reactant overhead. For avoidance of contamination of the low boiler output with the reactant used, the reactant is preferably applied in the lower portion of the distillation column. The reactant used can also be dewatered in other ways:

- by means of an upstream dewatering distillation column or
- by treatment with a dehydrating agent, for example a molecular sieve, or
- by a membrane separation method, for example a pervaporation.

The reason why the dewatering is important is because the water present in the reactant can lead to irreversible damage to the catalyst in the reactor. The water present in the reactant leads to the formation of by-products and should therefore be strictly avoided. This dewatering step avoids the hydrolysis of the catalyst and the associated costs resulting from elevated catalyst use amounts and resulting from problems with solid precipitates. Moreover, the purity of the product is increased by a reduced proportion of by-products.

The reaction is effected in the reaction apparatus at a temperature in the range between 70° C. and 160° C., according to the system and operating pressure.

According to the invention, the reaction temperature can be reduced in order to minimize the formation of compounds of the formula (IV). Preference is given to reducing the temperature to 80-120° C., more preferably to temperatures between 80° C. and 90° C. In order to achieve maximum completeness of conversion, reduced pressure is therefore employed. In a continuous mode of operation, the conversion is preferably effected in a tank cascade. All cascade stages can work under reduced pressure; preferably, the pressure is reduced in the last stage of the cascade.

Preference is given to working under a vacuum between 900 and 0 bar.

According to the invention, the decrease in the residence time can also lead to a reduction in the content of compounds of formula (IV) in the end product.

Residence times between 0.1 and 11 h, preferably between 1 and 5 h, lead to a noticeable reduction in the content of compounds of formula (IV) in the end product.

For a sufficiently high conversion in spite of a reduced residence time, it is necessary that more active catalysts be used or/and that the amount of catalyst be increased.

To increase the reaction rate, the alcohol released in the reaction is drawn off from the reaction mixture by means of a distillation column, optionally also as an azeotrope with the alcohol. This can be effected either at atmospheric pressure or under reduced pressure.

The reaction mixture, consisting for the most part of the N,N-(di)alkylaminoalkyl(meth)acrylamide or N,N-(di)alkylaminoalkyl (meth)acrylate product, unconverted (meth)acrylate and reactant, and small amounts of alcohol, the catalyst, the polymerization inhibitors and a proportion of by-products, after a reactor residence time of about 0.5-4 hours, preference being given to a residence time of 1-2 hours, is fed to a continuously operated falling-film evaporator. The vapours from the falling-film evaporator are fed to a low boiler distillation column. In this column, under reduced pressure, preferably in the range of about 1 mbar-500 mbar, the components that are low-boiling in relation to the product, predominantly product alcohol and unconverted reactant (meth)acrylate and reactant amine or alcohol, are removed. These are drawn off via the top of the distillation column and recycled into the reactor region or into the distillation column. This circulation stream achieves a high conversion based on the reactants and the overall process.

The crude product which is still contaminated with catalyst, polymerization inhibitor and high-boiling by-products and is obtained in the output from the falling-film evaporator contains preferably >80% by weight of product and, for workup, is fed to a further vacuum distillation stage which works within the preferred pressure range between 0.1 and 200 mbar. Here, the pure product is removed by distillation as the top product. Suitable apparatuses that are known for this purpose are falling-film, thin-film and short-path evaporators.

The preparation of the N,N-(di)alkylaminoalkyl(meth)acrylamides or N,N-(di)alkylaminoalkyl (meth)acrylates may optionally be followed downstream by a purifying distillation system which can also be operated under reduced pressure, for example at 500-0.1 mbar. This is necessary especially when a particularly good removal of the high-boiling secondary components formed in the process is to be effected.

The N,N-(di)alkylaminoalkyl(meth)acrylamide or N,N-(di)alkylaminoalkyl (meth)acrylate prepared in accordance with the invention, having a low content of compounds of the formula (IV), can be reacted with an alkyl halide or alkyl sulphonate, preferably with methyl chloride, to give the corresponding quaternary ammonium salt.

N,N-(Di)alkylaminoalkyl(meth)acrylamide or N,N-(di)alkylaminoalkyl (meth)acrylate and the quaternary ammonium salts thereof, having a low content of compounds of the formula (IV), are particularly suitable for the preparation of polymers which are brought into solution or else are polymerized in solution or as an emulsion or dispersion.

Preference is given to the use of N,N-(di)alkylaminoalkyl (meth)acrylamide or N,N-(di)alkylaminoalkyl (meth)acrylate having a content of the compound of the formula (IV) of less than 1200 ppm prepared according to Claim 1 which are used for polymerization in the form of bulk polymerization, solution polymerization, dispersion polymerization or emulsion polymerization, and find use as thickeners, gelling agents, haircare compositions (conditioning polymers), fixatives, styling polymers, film formers, household/industrial and institutional cleaning, flocculants, water clarifiers, paper auxiliaries/additives, printing inks, flow improvers in the oil & gas industry and as gas hydrate inhibitors, etc.

Preference is likewise given to the use of N,N-(di)alkylaminoalkyl(meth)acrylamide or N,N-(di)alkylaminoalkyl (meth)acrylate having a content of the compound of the formula (IV) of less than 1200 ppm prepared according to Claim 1 for conversion to quaternary ammonium salts which are used for polymerization and find use as thickeners, gelling agents, haircare compositions (conditioning polymers), fixatives, styling polymers, film formers, household/industrial and institutional cleaning, flocculants, water clarifiers, paper auxiliaries/additives, printing inks, flow improvers in the oil & gas industry and as gas hydrate inhibitors, etc.

The process according to the invention is elucidated in detail by the examples which follow, without being restricted thereto.

Having generally described this invention, a further understanding can be obtained by reference to certain specific examples which are provided herein for purposes of illustration only, and are not intended to be limiting unless otherwise specified.

EXAMPLES

Example 1

Synthesis of N,N-dimethylaminopropylmethacrylamide (DMAPMA) with Exclusion of Oxygen For continuous preparation of N,N-dimethylaminopropylmethacrylamide, the apparatus was operated under a nitrogen atmosphere. Into the 1st reaction tank were metered 200 kg/h of pre-activated catalyst feed having a content of 2.0% by weight of isopropyl titanate, 5.0% by weight of dioctyltin oxide from the distillation column and 144 kg/h of N,N-dimethylaminopropylamine (DMAPA). The pre-activation was conducted in a stirred tank at 110° C. for 2 h. In addition, the circulation return stream from the top of the low boiler distillation column flowed continuously to the 1st reaction tank via the distillation column (400 kg/h with the composition of 70% by weight of reactant methacrylate, and methanol, DMAPA and by-products). The molar MMA: DMAPA ratio in the reactor feed was 1.8:1. In addition, the vapours from the stirred tank which had been freed of methanol in the distillation column entered the 1st reaction tank via the bottom of the column. Under these reaction conditions (pressure about 500 mbar), a reaction temperature of 105° C. was established in the 1st reaction tank. The reaction temperatures in the 2nd and 3rd reaction tanks were 115° C. and 125° C. respectively. The distillate draw rate from the distillation column was 110 kg/h.

The output from the 1st reaction tank ran into the 2nd reaction tank and the output from the 2nd reaction tank ran into the 3rd reaction tank. The vapours from the individual reaction tanks were supplied continuously to a distillation column.

The output from the 3rd reaction tank continuously entered the thin-film evaporator of a low boiler column in which unconverted DMAPA, methyl methacrylate (MMA) and methanol were drawn off as distillate (400 kg/h) and fed back to the distillation column as circulation return stream. The bottoms output from the thin-film evaporator of the low boiler column was 230 kg/h and had the following composition: 98.5% by weight of DMAPMA, <1% low boilers, about 0.5% high boilers and 130 ppm of N-allylmethacrylamide.

Example 2

Synthesis of DMAPMA with Exclusion of Oxygen

The crude ester was prepared according to Example 1.

The vapours from the individual reaction tanks were supplied continuously to a distillation column.

The output from the 3rd reaction tank continuously entered the thin-film evaporator of a low boiler column in which unconverted DMAPA, MMA and methanol were drawn off as distillate (400 kg/h) and fed back to the distillation column as circulation return stream. The bottoms output from the thin-film evaporator of the low boiler column was 230 kg/h and had the following composition: 98.3% by weight of DMAPMA, <1% low boilers, about 0.7% high boilers and 240 ppm of N-allylmethacrylamide.

Comparative Example 1

Synthesis of DMAPMA under Oxygen

For continuous preparation of N,N-dimethylaminopropylmethacrylamide, into the 1st reaction tank were metered 200 kg/h of pre-activated catalyst feed having a content of 2.0% by weight of isopropyl titanate, 5.0% by weight of dioctyltin oxide from the distillation column and 144 kg/h of N,N-dimethylaminopropylamine (DMAPA). The pre-activation was conducted in a stirred tank at 110° C. for 2 h. In addition, the circulation return stream from the top of the low boiler distillation column flowed continuously to the 1st reaction tank via the distillation column (400 kg/h with the composition of 70% by weight of reactant methacrylate, and methanol, DMAPA and by-products). The molar MMA: DMAPA ratio in the reactor feed was 1.8:1. In addition, the vapours from the stirred tank which had been freed of methanol in the distillation column entered the 1 st reaction tank via the bottom of the column. Under these reaction conditions (pressure about 500 mbar), a reaction temperature of 138° C. was established in the 1st reaction tank. The reaction temperatures in the 2nd and 3rd reaction tanks were 143° C. and 155° C. respectively. The distillate draw rate from the distillation column was 110 kg/h.

The output from the 1st reaction tank ran into the 2nd reaction tank and the output from the 2nd reaction tank ran into the 3rd reaction tank.

The vapours from the individual reaction tanks were supplied continuously to a distillation column.

The output from the 3rd reaction tank continuously entered the thin-film evaporator of a low boiler column in which unconverted DMAPA, MMA and methanol were drawn off as distillate (400 kg/h) and fed back to the distillation column as circulation return stream. The bottoms output from the thin-film evaporator of the low boiler column was 240 kg/h and had the following composition: about 90% by weight of DMAPMA, 0.1% by weight of DMAPA, 0.16% by weight of N-allylmethacrylamide and a greater proportion of high-boiling components and traces of the reactants.

The crude product was subsequently worked up in a two-stage distillation.

Example 3

Laboratory study of the effect of oxygen on the formation of the compound of the formula (IV)

DMAPMA was stabilized with a suitable amount of the stabilizers mentioned, and about 10 g of the stabilized DMAPMA in each case were introduced into test tubes. Each test tube contains an inlet tube for introduction of air or nitrogen. The samples were then heated in different oil baths to 110° C./120° C./130° C./140° C. and 150° C., and air or nitrogen was introduced with a gas flow rate of about 0.75 l/h in each case over a period of 48 h. The samples were cooled and analysed by GC. The N-allylmethacrylamide content in DMAPMA was shown in GC area % in the table below.

| Temperature [° C.] | N-Allylmethacrylamide content in DMAPMA after 48 h/under air [GC area %] | N-Allylmethacrylamide content in DMAPMA after 48 h/under nitrogen [GC area %] |
| --- | --- | --- |
| 110 | 1.69 | 0.34 |
| 120 | 7.87 | 0.33 |
| 130 | 11.08 | 0.32 |
| 140 | 21.97 | 0.32 |
| 150 | 23.54 | 0.33 |

Example 4

Determination of the Limiting Concentration

Preparation of a copolymer from DMAPMA and N-allylmethacrylamide:

The DMAPMA (containing 130 ppm of N-allylmethacrylamide) was concentrated by the addition of N-allylmethacrylamide to a total concentration of N-allylmethacrylamide in the mixture of 300 ppm, 400 ppm, 500 ppm, 600 ppm, 700 ppm, 800 ppm, 1000 ppm, and 1200 ppm. (N-Allylmethacrylamide, from ABCR, Karlsruhe, Germany, batch: 1300868)

Subsequently, 10 g in each case were initiated with 0.2% AIBN and polymerization was effected at 70° C. in test tubes in a water bath within 3 h. The test tubes were cooled to room temperature overnight and then the glass was removed. A piece of polymer was taken from the solution.

Preparation of Aqueous Solutions:

The respective pieces of polymer were weighed into 125 ml wide-neck glass bottles and admixed with water to give a concentration of 3% or 5%. The solubility was checked for completeness after 96 h.

The viscosity of the homogeneous solutions was measured after 96 h by means of a Brookfield viscometer with a small-sample adapter (measurement apparatus for solutions having low viscosity).

| N-Allylmethacrylamide content | Viscosity [3% in H$_2$O] | Viscosity [5% in H$_2$O] |
| --- | --- | --- |
| 130 ppm | 24 mPa * s | 35 mPa * s |
| 300 ppm | 28 mPa * s | 37 mPa * s |
| 400 ppm | 31 mPa * s | 45 mPa * s |
| 500 ppm | 33 mPa * s | 51 mPa * s |
| 600 ppm | 33 mPa * s | 60 mPa * s |
| 700 ppm | Not measurable* | Not measurable* |
| 800 ppm | Not measurable* | Not measurable* |

*The viscosity was not measurable owing to the insolubility of the polymers.

European patent application EP16176555 filed Jun. 28, 2016, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing N,N-(di)alkylaminoalkyl (meth)acrylamide or N,N-(di)alkylaminoalkyl (meth)acrylate, said process comprising:
   reacting, in a liquid phase, an alkyl (meth)acrylate with an amine or an alcohol to prepare a product that comprises said N,N-(di)alkylaminoalkyl (meth)acrylamide or N,N-(di)alkylaminoalkyl (meth)acrylate;
   wherein the oxygen concentration is <1000 ppm in the liquid phase,
   wherein said N,N-(di)alkylaminoalkyl (meth)acrylamide or N,N-(di)alkylaminoalkyl (meth)acrylate have formula (I)

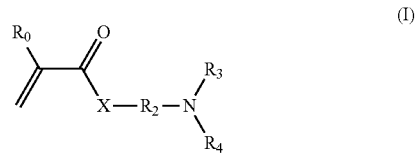

wherein
$R_0$ is hydrogen or methyl,
X is NH or O
$R_2$, is a linear, branched, or cyclic alkylene radical having 1-12 carbon atoms, or is an aryl radical that may also be substituted by at least one alkyl group,
$R_3$, $R_4$ are each a linear, branched, or cyclic alkyl radical having 1-12 carbon atoms, or is an aryl radical that may also be substituted by at least one alkyl group, and,
wherein the product has a content of less than 1200 ppm of a compound of formula (IV)

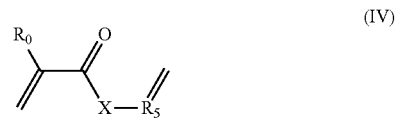

wherein $R_0$ is hydrogen or methyl,
X is NH or O
$R_5$ in each case is a linear, branched, or cyclic alkylene radical, an aryl radical which may also be substituted by at least one alkyl group, the linear, cyclic or branched alkyl radical having from 1-12 carbon atoms.

2. The process according to claim 1, wherein the N,N-(di)alkylaminoalkyl (meth)acrylamide or N,N-(di)alkylaminoalkyl (meth)acrylate or quaternary ammonium salts thereof have a content of less than 1200 ppm of the compound of the formula (IV) and are suitable for preparation of a soluble or non-coagulating polymer.

3. The process according to claim 2, wherein the N,N-(di)alkylaminoalkyl (meth)acrylamide or N,N-(di)alkylaminoalkyl (meth)acrylate or quaternary ammonium salts thereof have a content of less than 1000 ppm of the compound of the formula (IV).

4. The process according to claim 1, wherein the preparing is effected with exclusion of oxygen.

5. The process according to claim 1, wherein the preparing is conducted under a protective gas atmosphere.

6. The process according to claim 1, wherein a residence time is 0.1-11 h.

7. The process according to claim 1, wherein the preparing is conducted at temperatures between 70° C. and 160° C.

8. The process according to claim 6, wherein the preparing is conducted under reduced pressure.

9. The process according to claim 1, wherein the alcohol is removed during the reaction.

10. The process according to claim 1, wherein said reacting is conducted in the presence of at least one inhibitor selected from the group consisting of bis(2-methoxycarbonylpropyl) sulphide, N,N-diethylhydroxylamine, phenothiazine, 4-hydroxy-2,2,6,6-tetramethylpiperidinooxyl, N,N'-diphenyl-p-phenylenediamine and derivatives thereof.

11. N,N-(di)alkylaminoalkyl (meth)acrylamide or N,N-(di)alkylaminoalkyl (meth)acrylate obtained by a process according to claim 1.

12. The N,N-(di)alkylaminoalkyl (meth)acrylamide or N,N-(di)alkylaminoalkyl (meth)acrylate according to claim 11 which are suitable for polymerization in the form of bulk polymerization, solution polymerization, dispersion polymerization or emulsion polymerization.

13. A thickener, gelling agent, haircare composition, fixative, styling polymer, film former, household/industrial and institutional cleaning, flocculant, water clarifier, paper auxiliary/additive, printing ink, flow improver in the oil & gas industry or a gas hydrate inhibitor, comprising:
 the N,N-(di)alkylaminoalkyl (meth)acrylamide or N,N-(di)alkylaminoalkyl (meth)acrylate according to claim 11.

14. A method of preparing a quaternary ammonium salt, comprising:
 reacting the N,N-(di)alkylaminoalkyl (meth)acrylamide or N,N-(di)alkylaminoalkyl (meth)acrylate according to claim 11 with an alkyl halide or an alkyl sulphonate to give a quaternary ammonium salt which is suitable for polymerization.

* * * * *